United States Patent
Lunn et al.

[11] Patent Number: 5,997,508
[45] Date of Patent: Dec. 7, 1999

[54] EXPANDABLE PERCUTANEOUS INTRODUCER SHEATH

[75] Inventors: Peter A. Lunn, Beverly, Mass.; Steven B. Conner, East Kingston, N.H.

[73] Assignee: Medtronic, Inc., Minneapolis, Minn.

[21] Appl. No.: 08/623,094

[22] Filed: Mar. 28, 1996

[51] Int. Cl.[6] .................................................. A61M 5/178
[52] U.S. Cl. .......................................................... 604/164
[58] Field of Search ................................. 604/164, 264, 604/280, 248, 171; 606/198

[56] References Cited

U.S. PATENT DOCUMENTS

| | | | |
|---|---|---|---|
| 4,141,364 | 2/1979 | Schultze | 128/349 B |
| 4,451,256 | 5/1984 | Weikl et al. | 604/164 |
| 4,601,713 | 7/1986 | Fuqua | 604/280 |
| 4,634,433 | 1/1987 | Osborne | 604/171 |
| 4,899,729 | 2/1990 | Gill et al. | 128/3 |
| 4,921,479 | 5/1990 | Grayzel | 604/53 |
| 5,183,464 | 2/1993 | Dubrul et al. | 128/3 |
| 5,234,425 | 8/1993 | Fogarty et al. | 606/1 |
| 5,256,150 | 10/1993 | Quiachon et al. | 604/171 |
| 5,318,588 | 6/1994 | Horzewski et al. | 606/198 |
| 5,320,611 | 6/1994 | Bonutti et al. | 604/264 |
| 5,395,349 | 3/1995 | Quiachon et al. | 604/248 |
| 5,653,697 | 8/1997 | Quiachon et al. | 604/280 |

FOREIGN PATENT DOCUMENTS

EP 163 525  5/1985  European Pat. Off. ....... A61M 25/00

*Primary Examiner*—Manuel Mendez
*Attorney, Agent, or Firm*—David S. Brin; Dianne Plunkett Latham; Harold R. Patton

[57] ABSTRACT

An expandable percutaneous introducer sheath is disclosed which can be selectively enlarged to accommodate a range of sizes of interventional devices. The introducer sheath can retain an enlarged size without requiring an additional support member. The introducer sheath comprises an outer tube which contains expandable gaps along the length of the outer tube, expandable leaflets which are connected to the outer tube, an inner tubular member which is insertable into the outer tube, and a detent means to retain the enlarged size of the outer tube. The outer tube has a cross-sectional profile which is both kink resistant and minimizes the size of the puncture wound in the vasculature by providing a helix in the outer tube. An inner tubular member is inserted into the lumen of the outer tube and, because of the interference fit of the lumen outer tube to the outer diameter of the inner tubular member, the lumen of the outer tube enlarges at the expandable gaps.

12 Claims, 3 Drawing Sheets

EXPANDABLE PERCUTANEOUS INTRODUCER SHEATH

FIELD OF THE INVENTION

The present invention relates to percutaneous introducer sheaths and more particularly to a selectively expandable percutaneous introducer sheath which can accommodate the delivery of interventional devices of a range of sizes.

BACKGROUND OF THE INVENTION

Percutaneous transluminal coronary angioplasty (PTCA) is used to reduce arterial build-up of cholesterol fats or atherosclerotic plaque. A percutaneous introducer sheath is used to access the vascular system of the patient and acts as a means for introducing and positioning guiding catheters and other interventional devices within the patient. The introducer sheath is a tube-like member which is partially inserted into the vasculature at a puncture site, typically in either the femoral, brachial, or radial artery of the patient. The proximal, or working end, of the introducer sheath is accessible outside of the vasculature for the introduction of interventional devices through the sheath. Typically a guide wire is inserted through the introducer sheath and subsequently steered through the vascular system to the site of therapy. A guiding catheter, for example, can then be advanced through the introducer sheath and over the guide wire. The guiding catheter acts as a support conduit for therapeutic interventional devices such as balloon catheters. The balloon catheter is inserted through the guiding catheter and over the guide wire. The balloon at the distal end of the balloon catheter is inflated, causing the site of the arterial stenosis to widen.

An introducer sheath contains an access lumen for introduction of interventional devices, a luer hub for connection to syringes and other peripheral devices, and a hemostasis valve to prevent blood loss from the lumen of the introducer sheath. Typically, the PTCA procedure involves an initial diagnostic assessment of the extent and location of the arterial stenosis. To accomplish the diagnostic assessment, an introducer sheath is selected which will accommodate an angiographic catheter, which is typically of a 5F–7F (0.065–0.091 inches) outer diameter. Once the assessment is complete and the practitioner has determined that therapeutic intervention will be performed, the introducer sheath is typically replaced with a larger introducer sheath which will accommodate a guiding catheter of 8F–10F (0.104–0.130 inches) outer diameter. The practitioner will generally not insert the larger introducer sheath at the outset of the diagnostic assessment because of increased complications which result from the use of a larger puncture wounds in the vasculature.

Percutaneous introducer sheaths are known in the prior art. U.S. Pat. No. 5,318,588, issued to Horzewski et al., discloses, at column 12, lines 1–18:

"an intravascular sheath consisting of a shaft and a proximal hub. The shaft is composed of an inner tubular element 100 and an outer tubular element 101 . . . The inner tubular element 100 is designed to accommodate positive radial expansion over a specific range of dimensions. This is accomplished by constructing the element with overlapping surfaces and disposing at their interface a ratcheting mechanism consisting of a series of longitudinally disposed teeth 103 and a latch 102. The passage of a device therethrough of larger profile than the baseline luminal profile of the shaft engages latch 102 with successive teeth 103 and thereby radially expands the shaft of the sheath and maintains the shaft in its expanded configuration."

U.S. Pat. No. 5,183,464, issued to Dobrul et al., discloses, at column 9, lines 27–50, a percutaneous penetration apparatus which includes:

"an elongate dilation tube 10 and an elongate expansion member 12. The expansion member 12 includes an outer tube 30 and an inner rod 32. The dilation member 12 may be inserted into the axial lumen 22 of the dilation tube 10, resulting in expansion of the dilation tube. After the dilation tube 10 has been expanded, the inner rod 32 may be removed, leaving an expanded access channel 22 which is maintained by the outer tube 30."

U.S. Pat. No. 5,256,150, issued to Quiachon et al., discloses at column 3, lines 3–24:

"the large-diameter expandable sheath 11 consists of an elongate sheath tube 12 having proximal and distal extremities 13 and 14 and having a flow passage 16 having a maximum diameter extending therethrough . . . The distal extremity of the sheath tube, as shown in FIG. 4, is pleated or folded longitudinally to provide wraps or folds 17 for a distance of approximately 10 centimeters from the distal end to provide a distal extremity of reduced diameter, for example a reduction of the outside diameter from ⅜'"' to ³⁄₁₆" or approximately one-half the original size."

What is needed is a percutaneous introducer sheath which is adjustable in lumen size so that a range of interventional devices, from diagnostic to therapeutic, can be accommodated with a single percutaneous introducer sheath. Such a device would by design minimize the size of the puncture wound at the point of vascular access and would obviate the need to exchange from a smaller sheath for introduction of diagnostic devices, to a larger sheath, for therapeutic devices. Clinical studies have shown that the formation of thrombus and associated complications within the vasculature during PTCA procedures is attributed in part to the introduction and removal of interventional devices, such as introducer sheaths, from the vasculature. Consequently, if a single introducer sheath can be employed for both diagnostic and therapeutic procedures without the need to exchange the introducer sheath to accommodate therapeutic interventional devices, then patient complications during PTCA can be reduced.

SUMMARY OF THE INVENTION

It is an object of the invention to provide an expandable percutaneous introducer sheath which can be selectively enlarged to accommodate a range of sizes of interventional devices. Further, it is an object of the invention to provide an introducer sheath which can retain an enlarged size without requiring an additional support member. It is an additional object of the invention to provide an introducer sheath with a cross-sectional profile which is both kink resistant and minimizes the size of the puncture wound in the vasculature.

The present invention is accomplished by providing an apparatus comprising an outer tube which contains expandable gaps along the length of the outer tube, expandable leaflets which are connected to the outer tube, an inner tubular member which is insertable into the outer tube, and a detent means to retain the enlarged size of the outer tube. The inner tubular member is inserted into the lumen of the outer tube and, because of the interference fit of the lumen outer tube to the outer diameter of the inner tubular member, the lumen of the outer tube enlarges at the expandable gaps. The expandable leaflets provide a continuous lumen surface for the smooth passage of interventional devices. The detent means restrain the size of the lumen so that the inner tubular member can be removed once the lumen is enlarged to the desired size. The lumen is selectively adjustable by employing a range of sizes of the inner tubular member and inserting the desired inner tubular member size into the outer tube for expansion of the lumen.

DETAILED DESCRIPTION OF THE PREFERRED EMBODIMENTS

Figure 1:
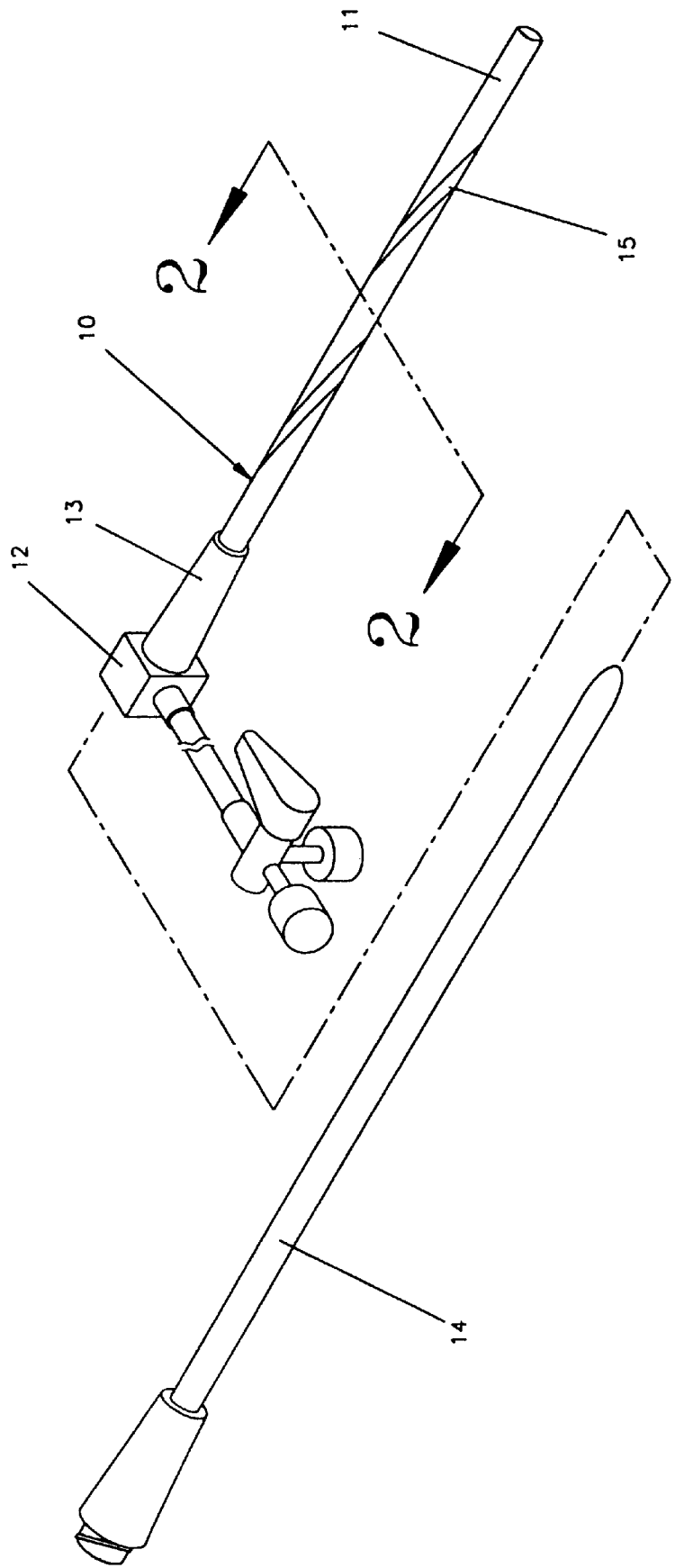
FIG. 1 is an isometric view of the preferred embodiment of an expandable percutaneous introducer sheath.

Referring to FIG. 1, the preferred embodiment of the applicants' expandable percutaneous introducer sheath 10 is depicted. The introducer sheath 10 includes an outer tube 11 which is preferably comprised of an extruded thermoplastic elastomer such as a 70D Shore durometer PEBAX®, a polyether block amide copolymer obtainable from Elf Atochem Corporation, Philadelphia Pa. Preferred dimensions for the outer tube 11 are a nominal inner diameter, or lumen, of 0.135 inches, a wall thickness of 0.005–0.015 inches, and a length of 10 to 100 cm. The preferred lumen size will accommodate interventional devices up to the 10 French (0.130 inches) size.

A luer hub 12 is bonded to the outer tube 11 using techniques such as solvent bonding or insert molding. The lumen of the introducer sheath 10 is in fluid communication with the lumen of the luer hub 12. The lumen of the luer hub 12 is approximately 0.135 inches in diameter. The luer hub 12 is an industry standard ANSI connector to which devices such as syringes and the like may be connected to infuse drugs into the vasculature. Preferred materials for the luer hub 12 include thermoplastics such as MAGNUM® ABS, obtainable from the Dow Chemical Company, Midland, Mich. The luer hub 12 contains a hemostasis valve (not shown) to reduce the flow of blood from the vasculature through the introducer sheath 11. Details of the construction of a hemostasis valve may be obtained in U.S. Pat. No. 5,125,903, issued to McLaughlin et al.

A strain relief 13 is connected to the outer tube 11 and to the luer hub 12 to provide a stiffness transition to reduce the likelihood of flexural kinking at the junction between the outer tube 11 and the luer hub 12. The strain relief 13 may be injection molded and subsequently solvent bonded to the outer tube 11 and to the luer hub 12. Preferred materials for the strain relief 13 include the 35D Shore durometer PEBAX®.

An inner tubular member 14 is provided which is inserted into the lumen of the introducer sheath 10 to expand the lumen and subsequently removed after expansion of the lumen. The inner tubular member 14 includes a tapered outer diameter of 6 French (0.078 inches nominally ) at the proximal end and 5 French (0.065 inches) at the distal end. The tapered distal end, which is approximately 2 cm in length, of the inner tubular member 14 eases the trauma to the patient when inserting the introducer sheath 10 into the vasculature. Preferably, the inner tubular member 14 is provided in a range of sizes including 7F (0.091 inches), 8F (0.105 inches), 9F (0.117 inches), and 10F. All sizes of the inner tubular member include a tapered distal end which is approximately 1F (0.013 inches) smaller in outer diameter than the proximal end. The range of sizes allows the practitioner to selectively expand the lumen of the introducer sheath 10 to accommodate a range of sizes of catheters. The choice of size of the inner tubular member 14 is based upon the desired size of the catheter. For example, for a desired catheter size of 7F, the appropriate size for the inner tubular member 14 is a proximal outer diameter of 7F.

The inner tubular member 14 also includes an inner diameter of approximately 0.040 inches to accommodate a range of guide wire sizes. The inner tubular member 14 is preferably comprised of a 72D PEBAX® which is extruded and subsequently drawn through a sizing die to produce the tapered outer diameter. The overall length of the inner tubular member 14 is 5–10 cm longer than the introducer sheath 10 to allow for the tapered distal end of the inner tubular member 14 to protrude distally of the distal end of the outer tube 11.

The outer tube 11 is preferably wound in a continuous helix 15 from the proximal to distal end of the outer tube 11. The preferred pitch of the continuous helix 15 is approximately 5 cm. The winding of the helix 15 in the outer tube 11 reduces the size of the lumen of the outer tube 11 from the extruded size of 0.135 inches to an unexpanded size of approximately 0.078 inches. The helix 15 in the outer tube 11 results in improved kink resistance over a longitudinal folding of the outer tube 11 because the stress concentration of the cross-section of the outer tube 11 is oriented off of the longitudinal axis of the outer tube 11. Thus, the resistance of the outer tube to a bending or flexural kink, such as would be encountered upon pushing the distal end of the outer tube 11 into the vasculature, is improved with the helix 15. Further, the helix 15 reduces the cross-sectional profile of the outer tube 11, thereby reducing the trauma to the patient upon initial insertion of the introducer sheath 10 into the vasculature.

Figure 2:
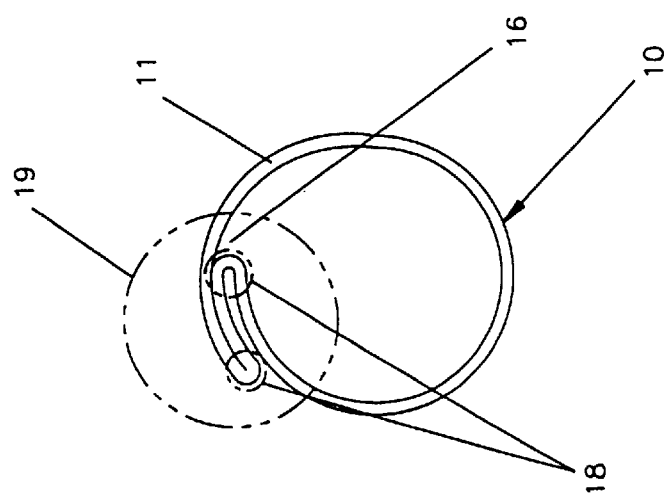
FIG. 2 is a cross-sectional view along Section 2—2 of FIG. 1 showing the lumen of the introducer sheath in the unexpanded state.

Referring to FIG. 2, the applicants' expandable percutaneous introducer sheath is shown in a cross-sectional view along Section 2—2 of FIG. 1 showing the lumen of the introducer sheath 10 in the unexpanded state prior to insertion of the inner tubular member 14 of FIG. 1. The forming of the helix 45 in the outer tube 11 results in the formation of expandable gaps 16 within the lumen of the outer tube 11. The forming of the helix 15 in the outer tube 11 also results in the formation of expandable leaflets 17 in the outer tube 11. The expandable leaflets 17 comprise a lobe 19 of material from the outer tube 11. In an alternative embodiment, the expandable leaflets 17 comprise a separate material which is bonded t o the outer tube and which spans the expandable gaps 16.

In the preferred embodiment, the length of the lobe 19 is approximately the difference in circumference between the unexpanded lumen and the expanded lumen of the outer tube 11. For an unexpanded lumen of 0.078 inches and an expanded lumen of 0.135 inches, the lobe length is approximately:

$$^1(0.135-0.078)=0.179 \text{ inches.}$$

The above calculation assumes purely elastic behavior of the materials comprising the outer tube 11. As will be discussed below, the assumption of purely elastic behavior of the outer tube 11 is flawed and therefore, the above calculation is only a rough approximation for the lobe length.

To expand the lumen of the outer tube 11, an inner tubular member 14 is selected to correspond to the desired lumen size of the outer tube 11. Upon insertion of the inner tubular member 14 of FIG. 1, the inner tubular member 14 forces the length of the expandable gaps 16 of the outer tube 11 to expand because of the interference fit of the inner tubular member 14 to the unexpanded lumen of the outer tube 11. As a result, the lumen of the outer tube 11 expands.

To deliver interventional devices through the expanded lumen of the outer tube 11, the inner tubular member 14 of FIG. 1 is removed from the lumen. To ensure that the lumen of the outer tube 11 remains expanded after removal of the inner tubular member 14 of FIG. 1, detents 18 retain the expanded size of the lumen. The winding of the outer tube 11 to create the helix 15 creates a strain hardening of the materials comprising the outer tube 11. The strain hardening is most pronounced in the region of the apex of the expandable leaflets 17 and at the junction of the expandable leaflets 17 and the outer tube 11 where the materials of the outer tube 11 are deformed into 180 degree bends. It is in strain hardened regions of the expandable leaflet 17 that the effect of the detents 18 is believed to be attained. In an alternative embodiment, the detents 18 form with the expandable leaflets 17 a ratchet and pawl mechanism to retain the expanded lumen of the outer tube 11.

In the preferred embodiment, when the inner tubular member 14 is inserted, the interference fit of the inner tubular member 14 with the lumen of the outer tube 11 causes increased strain hardening of the expandable leaflets 17 as the lumen of the outer tube 11 expands. The detents 18 are resistive to elastic recoil of the outer tube 11 because of the plastic deformation which has occurred in the expandable leaflets 17.

Figure 3:
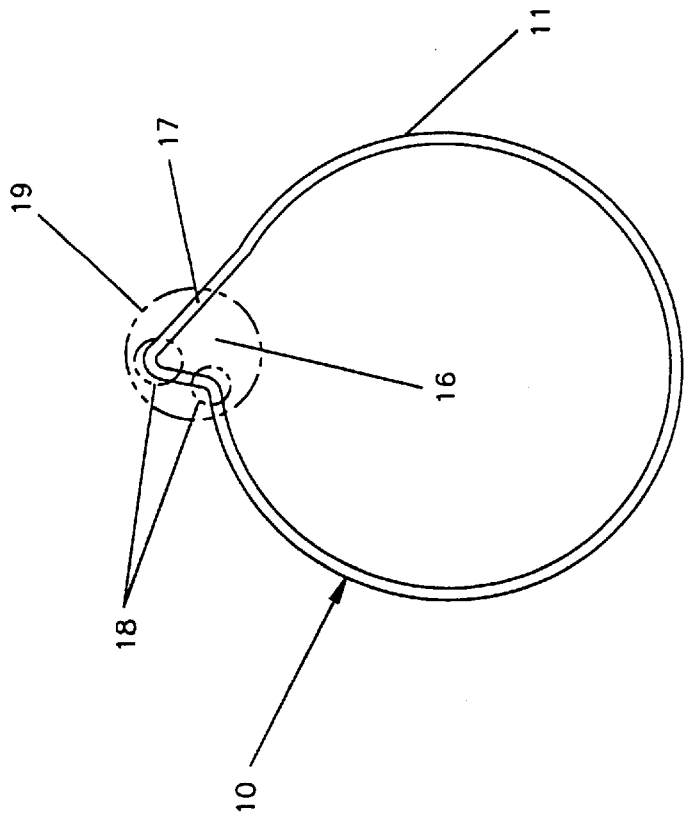
FIG. 3 is a cross-sectional view along Section 2—2 of FIG. 1 showing the lumen of the introducer sheath in the expanded state.

Referring to FIG. 3, the applicants' percutaneous introducer sheath 10 is shown in a cross-sectional view along Section 2—2 of FIG. 1 showing the lumen of the introducer sheath 10 in the expanded state after insertion and removal of the inner tubular member 14 of FIG. 1. The expandable leaflets 17 and the detents 18 are shown.

Figure 4:
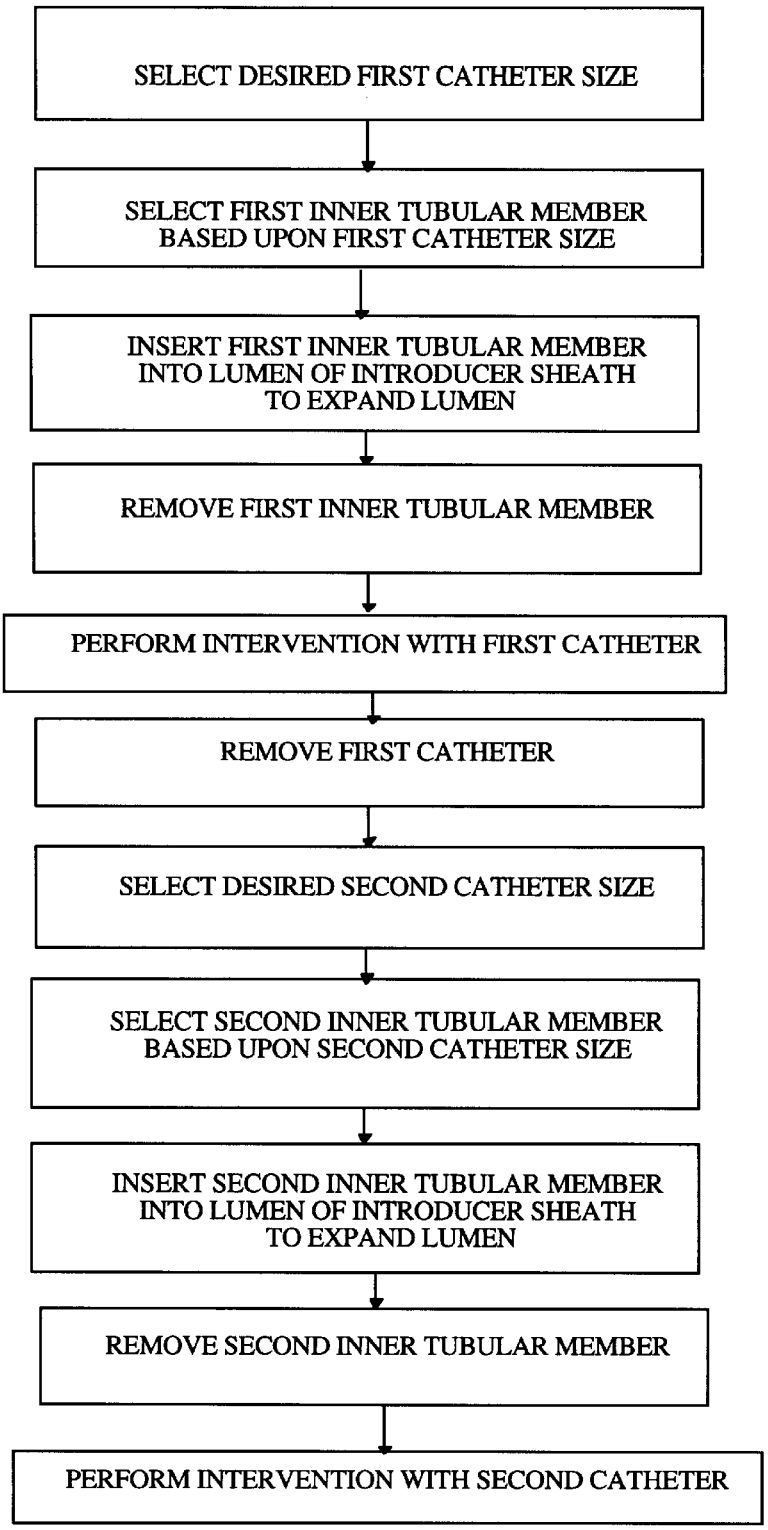
FIG. 4 depicts the method for utilizing applicants' expandable percutaneous introducer sheath in a flow chart.

Referring to FIG. 4, the method for utilizing applicants' expandable percutaneous introducer sheath is depicted in a flow chart. The method involves the initial selection of the size of the first catheter to be used in the patient. The first catheter is typically a diagnostic catheter of 5, 6, or 7F size. Based upon the desired first catheter size, the appropriate size for the first inner tubular member is selected. For a 6F diagnostic catheter, a first inner tubular member with a proximal outer diameter of 6F is selected.

The first inner tubular member is inserted into the lumen of the introducer sheath to expand the lumen of the introducer sheath to the size of the outer diameter of the first inner tubular member. The first inner tubular member is inserted in the lumen of the introducer sheath to a depth at which the tapered distal end of the first inner tubular member is distal of the distal end of the outer tube of the introducer sheath. This depth ensures a consistent expanded lumen size along the length of the introducer sheath. The first inner tubular member is then removed and the diagnostic catheter is inserted.

Upon completion of the diagnostic catheterization, the diagnostic catheter is removed. The practitioner typically selects a second catheter size for therapeutic treatment of the patient. A second inner tubular member is selected to correspond to the size of the second catheter size. For example, if the practitioner selects a 10F catheter size for therapy, a second inner tubular member with a 10F proximal outer diameter is selected. The second inner tubular member is inserted into the lumen of the introducer sheath to a depth at which the tapered distal end of the second inner tubular member is distal of the distal end of the outer tube of the introducer sheath. The second inner tubular member is then removed and the therapeutic catheter is inserted. This series of steps can be followed for subsequent catheter selections.

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10 | introducer sheath |
| 11 | outer tube |
| 12 | luer hub |
| 13 | strain relief |
| 14 | inner tubular member |
| 15 | helix |
| 16 | expandable gaps |
| 17 | expandable leaflets |
| 18 | detents |
| 19 | lobe |

What is claimed is:

1. An expandable percutaneous introducer sheath comprising:
    an outer tube, the outer tube having a proximal end, a distal end, and defining a lumen, the outer tube defining a expandable, longitudinally extending, helically arranged fold between the proximal end and the distal end, the expandable fold defining an overlap length, the overlap length decreasing in response to an outwardly directed force on the lumen of the outer tube, the lumen of the outer tube increasing in size in response to a decrease in the overlap length; and
    whereby the lumen of the outer tube, after increasing in size in response to a decrease in the overlap length, resists recoil after removal of the outwardly directed force on the lumen of the outer tube.

2. The expandable percutaneous introducer sheath according to claim 1 wherein the overlap length increases circumferentially about the outer tube.

3. The expandable percutaneous introducer sheath according to claim 1 wherein the expandable overlap is axially and circumferentially -spaced about the outer tube.

4. The expandable percutaneous introducer sheath according to claim 1 wherein the overlap is strain-hardened.

5. The expandable percutaneous introducer sheath according to claim 1 further comprising an inner tubular member, the inner tubular member having a proximal end and a distal end, the inner tubular member being insertable into the lumen of the outer tube, the inner tubular member, upon insertion into the lumen of the outer tube, exerting an outwardly directed force on the lumen of the outer tube.

6. The expandable percutaneous introducer sheath according to claim 5 wherein the distal end of the inner tubular member is tapered and sized to a smaller diameter than the lumen of the outer tube and the proximal end of the inner tubular member is sized to a larger diameter than the lumen of the outer tube.

7. The expandable percutaneous introducer sheath according to claim 5 wherein the removal of the inner tubular member removes the outwardly directed force on the lumen of the outer tube.

8. An expandable percutaneous introducer sheath comprising:
- an outer tube, the outer tube having a proximal end, a distal end, and defining a lumen, the outer tube defining a strain-hardened expandable longitudinally extending fold between the proximal end and the distal end, the expandable folds being arranged in a helix about the outer tube, the expandable fold defining an overlap length, the overlap length decreasing circumferentially about the outer tube in response to an outwardly directed force on the lumen of the outer tube, the lumen of the outer tube increasing in size in response to a decrease in the overlap length; and
- an inner tubular member, the inner tubular member having a proximal end and a distal end, the inner tubular member being insertable into the lumen of the outer tube, the inner tubular member, upon insertion into the lumen of the outer tube, exerting an outwardly directed force on the lumen of the outer tube, whereby the lumen of the outer tube, after increasing in size in response to a decrease in the overlap length, resists recoil after removal of the outwardly directed force on the lumen of the outer tube.

9. The expandable percutaneous introducer sheath according to claim 8 wherein the expandable folds form a continuous helical gap.

10. The expandable percutaneous introducer sheath according to claim 8 wherein the distal end of the inner tubular member is tapered and sized to a smaller diameter than the lumen of the outer tube and the proximal end of the inner tubular member is sized to a larger diameter than the lumen of the outer tube.

11. The expandable percutaneous introducer sheath according to claim 8 wherein the removal of the inner tubular member removes the outwardly directed force on the lumen of the outer tube.

12. An expandable percutaneous introducer sheath comprising:
- an outer tube, the outer tube having a proximal end, a distal end, and defining a lumen, the outer tube defining a continuous, expandable longitudinally extending, helically arranged fold between the proximal end and the distal end, the expandable fold defining an overlap length, the overlap length decreasing circumferentially about the outer tube in response to an outwardly directed force on the lumen of the outer tube, the lumen of the outer tube increasing in size in response a decrease in the overlap length; and
- an inner tubular member, the inner tubular member having a proximal end and a distal end, the distal end of the inner tubular member being tapered and sized to a smaller diameter than the lumen of the outer tube, the proximal end of the inner tubular member being sized to a larger diameter than the lumen of the outer tube, the inner tubular member being insertable into the lumen of the outer tube, the inner tubular member, upon insertion into the lumen of the outer tube, exerting an outwardly directed force on the lumen of the outer tube, the removal of the inner tubular member removing the outwardly directed force on the lumen of the outer tube, whereby the lumen of the outer tube, after increasing in size in response to a decrease in the overlap length, resists recoil after removal of the outwardly directed force on the lumen of the outer tube.

* * * * *